United States Patent [19]

Tanaka

[11] Patent Number: 5,640,714
[45] Date of Patent: Jun. 24, 1997

[54] LOWER LEG PROTECTION GARMENT FORMED FROM MATERIALS HAVING STRONG AND WEAK STRAINING FORCES

[75] Inventor: Masami Tanaka, Chiba-ken, Japan

[73] Assignee: Wacoal Corp., Kyoto-fu, Japan

[21] Appl. No.: 537,301

[22] Filed: Sep. 29, 1995

[30] Foreign Application Priority Data

Oct. 7, 1994 [JP] Japan .................................. 6-244159

[51] Int. Cl.⁶ .......................... A41D 13/00; A61F 13/00
[52] U.S. Cl. ............................. 2/22; 2/240; 602/62
[58] Field of Search .................................. 2/22, 24, 240, 2/16, 239, DIG. 9, 311, 320, 409; 602/62, 63, 60, 61, 64, 65, 66; 66/178 A, 178 R, 172 E

[56] References Cited

U.S. PATENT DOCUMENTS

| | | |
|---|---|---|
| 366,590 | 7/1887 | Lubin . |
| 2,283,278 | 5/1942 | Morse ................................. 2/240 |
| 3,322,118 | 5/1967 | Sotherlin ............................. 2/24 |
| 3,934,583 | 1/1976 | Hollingshead et al. ............ 128/165 |
| 4,166,460 | 9/1979 | Applegate ......................... 128/80 |
| 4,176,665 | 12/1979 | Terpening ........................ 128/165 |
| 4,832,010 | 5/1989 | Lerman .............................. 2/24 |
| 5,263,923 | 11/1993 | Fujimoto ........................... 602/62 |
| 5,367,708 | 11/1994 | Fujimoto ........................... 2/22 |
| 5,497,513 | 3/1996 | Arabeyre et al. .................. 2/22 |

FOREIGN PATENT DOCUMENTS

| | | |
|---|---|---|
| 0227566 | 9/1986 | European Pat. Off. . |
| 0272989 | 11/1987 | European Pat. Off. . |
| 2366809 | 10/1977 | France . |
| 766278 | 8/1954 | United Kingdom . |
| 2242818 | 8/1990 | United Kingdom . |

OTHER PUBLICATIONS

Copy of European Search Report dated Jan. 24, 1996.

*Primary Examiner*—C. D. Crowder
*Assistant Examiner*—Larry D. Worrell, Jr.
*Attorney, Agent, or Firm*—Merchant, Gould, Smith, Edell, Welter & Schmidt, P.A.

[57] ABSTRACT

A lower leg protection garment is compressingly worn on the surface of a human body, having a tube-like shape from the vicinity of the region just below the knee joint to the vicinity of the ankle. The garment has a portion with a strong straining force which covers at least a part of tuber calcaneus across the sole and extends to the vicinity of the region just below the knee joint covering at least a part of the both sides of the lower leg region, and a portion with a weak straining force in the portion at least one third of the area of the portion having the tube-like shape below the knee joint, reinforcing the lower leg region to provide protection against the ankle sprain or recurrence thereof, enabling anyone to wear appropriately to the proper orientation without skill, providing good wearing comfort.

13 Claims, 14 Drawing Sheets

LOWER LEG PROTECTION GARMENT FORMED FROM MATERIALS HAVING STRONG AND WEAK STRAINING FORCES

BACKGROUND OF THE INVENTION

1. Field of the Invention

The present invention relates to lower leg protection garments, and more specifically to a lower leg protection garment which is applied closely onto the surface of lower leg regions of a human body and provides taping functions primarily to reinforce body parts which are susceptible to cause sprain, blown muscle, torn muscle and other muscle injuries in sports activities, to reinforce body parts which have been previously injured and prevent the relapse of the injury, and to prevent muscle injury without hindering the physical exercise ability.

2. Description of the Prior Art

Conventionally in sports or training activities, articles specifically designed for prevention of an injury or an injury relapse, or taping treatments applied by swathing or sticking an elastic or non-elastic adhesive tape around a joint, muscle or ligament of a human body for treatment or prevention of muscle injury have been broadly utilized as an effective means to treat or prevent injuries. That is, such measures have been taken for injury prevention, prevention of pain caused by fatigue or relapse of such pain, first-aid treatments conducted at the spot immediately after the injury, and also for reinforcement or strengthening of the injured part after healing.

In addition to the above mentioned taping treatment, supporters having a tube-like shape made of stretchable, relatively thick, pile fabrics or rubber materials including neoprene are often used to compress human body regions, such as ankles or the vicinity of a knee joint inwardly from the circumference.

However, the above-mentioned conventional taping method requires skill and if the treatment is applied inadequately, it not only fails to accomplish the prevention or treatment of injuries but also can produce an adverse effect on the muscle area, such as disturbing physical movements, and increasing susceptibility to blood circulation disorders or nervous disorders. Therefore the taping method can be applied only by those who are skilled in the method but not by those who are not.

As for the latter supporter method, such supporters can be worn easily, but since they simply compress strongly a certain region from the circumference they often prevent proper blood circulation to cause discomfort and sometimes result in blood circulation disorders, or increased susceptibility to injury due to dulled sensitivity of the vicinity of the region. Also, since a supporter for a heel, in general, extends only to the ankle, it cannot apply the upward force to the heel to stabilize the region. Besides, since materials such as a rubber material including neoprene or a thick pile material are used, there are problems such as influence on physical movements in sports caused by difficulty of moving the part applied with a supporter, or deteriorated ventilation and stuffiness.

SUMMARY OF THE INVENTION

It is an object of the present invention to provide a lower leg protection garment to reinforce a lower leg region to prevent the ankle sprain or relapse thereof, which can be put on easily by anybody onto an appropriate portion, and to be easily put on, providing wearing comfort.

In the below mentioned preferable embodiments of the present invention, the following objects may be included according to each embodiment in addition to the above mentioned objects.

It is another object of the present invention to provide a lower leg protection garment without discomfort in physical movements, providing further better wearing comfort.

It is a further object of the present invention to provide a lower leg protection garment to achieve the above mentioned objects without disturbing movements such as contraction of a gastrocnemius, which is the most projecting muscle in the lower leg region.

It is another object of the present invention to provide a lower leg protection garment which further has a function not to disturb movements of an Achilles' tendon.

It is a further object of the present invention to provide a lower leg protection garment which further facilitates the prevention of inflammation of the plantar fascia more effectively.

It is another object of the present invention to provide a lower leg protection garment which holds an ankle more firmly to further reinforce the sprain prevention function.

It is a further object of the present invention to provide a lower leg protection garment which further prevents inflammation of plantar fascia more effectively and holds an ankle securely to further reinforce the sprain prevention function.

It is another object of the present invention to provide a lower leg protection garment which can hold a heel or an ankle more firmly.

It is a further object of the present invention to provide a lower leg protection garment which has an well balanced function of the above mentioned protection function with an appropriate straining force and a good wearing comfort without deteriorating wearing feeling.

It is another object of the present invention to provide a lower leg protection garment which can be more easily put on without slackness or disturbing muscle movements in the applied region.

It is a further object of the present invention to provide a lower leg protection garment which can be more easily produced.

It is another object of the present invention to provide a lower leg protection garment which is lightweight, has further better feeling, and good ventilation and is more easily put on by the wearer.

It is a further object of the present invention to provide a lower leg protection garment which is more easily put on, lightweight, has further better feeling and good ventilation, and is more easily produced.

It is another object of the present invention to provide a lower leg protection garment which provides a sufficient straining force, good fittability to a human body, is lightweight, without disturbing muscle movements, has a further better feeling and wearing comfort, and good ventilation.

It is a further object of the present invention to provide a lower leg protection garment which can more easily be put on in the appropriate orientation to have the desired condition without susceptibility of sliding down.

The present invention relates to a lower leg protection garment to be compressingly worn on the surface of a human body, having a tube-like shape from the vicinity of the region just below the knee joint to the vicinity of the ankle, comprising a portion with a strong straining force which covers at least a part of tuber calcaneus across the sole and extends to the vicinity of the region just below the knee joint covering at least a part of the both sides of the lower leg region, and at least one third of the area of the portion having the tube-like shape below the knee joint is formed with a portion with a weak straining force.

It is preferable that in a lower leg protection garment of the present invention, the portion with a strong straining force which covers at least a part of tuber calcaneus across the sole and extends to the vicinity of the region just below the knee joint, avoids the malleolus medialis and a malleolus laterails.

It is preferable that in a lower leg protection garment of the present invention, the portion with a strong straining force which covers at least a part of tuber calcaneus across the sole and extends to the vicinity of the region just below the knee joint, covers the regions along the vicinity of the both sides of the motor point of the gastrocnemius longitudinally, and the portion to cover the motor point of the gastrocnemius is formed with the portion with a weak straining force.

It is preferable that in a lower leg protection garment of the present invention, a portion covering the central part of the Achilles' tendon is formed with a portion with a weak straining force.

It is preferable that in a lower leg protection garment of the present invention, the portion with a strong straining force further covers at least a part of the plantar arch across the sole extending to at least a part of the dorsum pedis so that the portion with the strong straining force forms a further tube like part, and the portion with the strong straining force has a width at the sole of 3 cm or more.

It is preferable that in a lower leg protection garment of the present invention, the portion with a strong straining force further covers the front side of the ankle, so that the portion with the strong straining force forms a further tube-like part.

It is preferable that in a lower leg protection garment of the present invention, the portion with a strong straining force further covers at least a part of the plantar arch across the sole with a width at the sole of at least 3 cm and extends to at least a part of the dorsum pedis so that the portion with the strong straining force forms a further tube-like part, and extends further from the dorsum pedis to the front side of the ankle to cover the ankle so that the portion with the strong straining force forms a further tube-like part.

It is preferable that in a lower leg protection garment of the present invention, support bones are further provided in the lower leg region applied on at least a part of heel bone, or the vicinity of the ankle, avoiding the malleolus medialis and the malleolus lateralis regions.

It is preferable that in a lower leg protection garment of the present invention, the straining force of the portion with a strong straining force is in the range of 100 to 400 gf.

It is preferable that in a lower leg protection garment of the present invention, the straining force of the portion with a weak straining force is in the range of 30 to 250 gf.

It is preferable that in a lower leg protection garment of the present invention, the main body comprises a material with a weak straining force and a material with a strong straining force is further superimposed on the surface and/or the underside of the material with a weak straining force to provide a portion with a strong straining force.

It is preferable that in a lower leg protection garment of the present invention, a portion with a weak straining force comprises an all ways stretch tricot.

It is preferable that in a lower leg protection garment of the present invention, a material with a weak straining force, used when a material with a strong straining force is further superimposed on the surface and/or the underside of the material with a weak straining force to provide a portion with a strong straining force, is an all ways stretch tricot.

It is preferable that in a lower leg protection garment of the present invention, a portion with a strong straining force comprises a spandex power net.

It is preferable that in a lower leg protection garment of the present invention, a crotch portion is provided to form a pants-like shape.

The lower leg protection garment of the present invention comprises a portion with a strong straining force which covers at least a part of tuber calcaneus across the sole and extends to the vicinity of the region just below the knee joint covering at least a part of the both sides of the lower leg region. Thus the portion with a strong straining force extends from at least a part of tuber calcaneus to the vicinity of the region just below the knee joint, to provide a force to firmly lift the heel portion upward to stabilize the portion. The present lower leg protection garment thus can help prevent the inversion and the eversion of the ankle (Each term refers to bending the ankle toward the center of the body or inward, and bending the ankle outward, respectively. In particular, sprain often arises from the inversion of the ankle.) to provide the sprain prevention effect. This also enables easy wearing like putting on socks to the proper orientation for having the tube-like shape at least from the vicinity of the region just below the knee joint to the vicinity of the ankle, without the skill required in taping treatments such as the skill to know the portion to adhere or the portion to strongly adhere without the risk of the blood circulation disorder or nervous disorder caused by strongly applying taping. The present invention has a good wearing comfort since at least one third of the area of the portion having the tube-like shape below the knee joint is formed with a portion with a weak straining force, allowing the easy extension of the material and not compressing the leg region strongly unlike an embodiment comprising the whole portion with a portion with a strong force.

According to one of the preferable embodiments of the lower leg protection garment of the present invention, a portion with a strong straining force covers at least a part of the tuber calcaneus across the sole and extends to the vicinity of the region just below the knee joint, avoiding the malleolus medialis and a malleolus lateralis. Such a lower leg protection garment provides further better wearing comfort by reducing the chance of generating discomfort by locating the portion with a strong straining force to avoid the malleolus medialis and the malleolus lateralis, to prevent friction between the malleolus region and the protection garment having a portion with a strong straining force which compresses the malleolus region during sports activities.

According to the preferable embodiments of the lower leg protection garment of the present invention, the portion with a strong straining force covers at least a part of tuber calcaneus across the sole and extends to the vicinity of the region just below the knee joint along the vicinity of the both sides of the motor point of the gastrocnemius longitudinally, and the portion to cover the motor point of the gastrocnemius is formed with the portion with a weak straining force. Such a lower leg protection garment provides a further better wearing comfort by reinforcing the lower leg region to prevent the occurance or relapse of ankle sprain without disturbing the movements such as contraction of the gastrocnemius, which is the most projecting muscle among the muscles of the lower leg region, and allows anybody to put on the garment with the proper orientation.

According to one of the preferable embodiments of the lower leg protection garment of the present invention, a portion covering the central part of the Achilles' tendon is formed with a portion with a weak straining force. Such a lower leg protection garment provides a further good wearing comfort by reinforcing the lower leg region to prevent the occurance or relapse of the ankle sprain without disturbing the movements of the Achilles' tendon, and allows anybody to put on the garment with the proper orientation.

According to one of the preferable embodiments of the lower leg protection garment of the present invention, the portion with a strong straining force further covers at least a part of the plantar arch across the sole and extends to at least a part of the dorsum pedis so that the portion with the strong straining force forms a further tube-like part, and the width of the tube-like part with the strong straining force at the sole is 3 cm or more. Such a lower leg protection garment further has the function of preventing the inflammation of plantar fascia more effectively by having the portion at the plantar arch with a strong straining force of at least 3 cm width.

According to one of the preferable embodiments of the lower leg protection garment of the present invention, the tube-like portion with a strong straining force further covers the front side of ankle so that the portion with a strong straining force forms further a tube-like part. Thus, a lower leg protection garment providing a further reinforced sprain prevention effect by firmly holding and stabilizing the ankle can be provided.

According to one of the preferable embodiments of the lower leg protection garment of the present invention, a portion with a strong straining force further covers at least a part of the plantar arch across the sole with a width at the sole of at least 3 cm and extends to cover at least a part of the dorsum pedis to form a further tube-like shape, and further extends from the dorsum pedis to the front side of the ankle to cover the ankle to form a tube-like shape. Thus, a lower leg protection garment providing effective prevention effect of the inflammation of plantar fascia, holding the ankle firmly, and providing reinforced sprain prevention effect can be provided.

According to one of the preferable embodiments of the lower leg protection garment of the present invention, support bones are provided at least in the area of a part of the heel bone, or the vicinity of the ankle in the lower leg region, avoiding the malleolus medialis and the malleolus lateralis regions. Such a lower leg protection garment provides a further reinforced sprain prevention effect by fixing heel or the ankle region more firmly.

According to one of the preferable embodiments of the lower leg protection garment of the present invention, the straining force of the portion with a strong straining force is in the range of 100 to 400 gf. Thus, a lower leg protection garment which balances the protection effect of the lower leg region and good wearing comfort by having the straining force of a portion with a strong straining force in the above mentioned range, which is an appropriate straining force to provide the sprain prevention effect for protection but not too strong in terms of wearing comfort, can be provided.

According to one of the preferable embodiments of the lower leg protection garment of the present invention, the straining force of the portion with a weak straining force is in the range of 30 to 250 gf. Such a lower leg protection garment does not disturb the muscle movements of the region covered with the portion with a weak straining force, allowing easy expansion of the garment during wearing by not having a too strong straining force, but without the susceptibility of loosening the garment during wearing by not having a too weak straining force, can be provided.

According to one of the preferable embodiments of the lower leg protection garment of the present invention, the main body comprises a material with a weak straining force, and a material with a strong straining force is further superimposed to the surface and/or the underside of the material with a weak straining force to provide a portion with a strong straining force. Such a lower leg protection garment can be easily produced by only forming a base material of the protection garment main body with a material with a weak straining force, and fixing a material with a strong straining force to the surface and/or the underside of the base material in the necessary region by an appropriate means such as stitching or adhesion without the complicated, time consuming operation of alternately seaming a portion with a weak straining force and a portion with a strong straining force.

According to one of the preferable embodiments of the lower leg protection garment of the present invention, a portion with a weak straining force comprises an all ways stretch tricot, which is a knit fabric thinner than pile fabric or neoprene used in conventional supporters. Thus a lower leg protection garment having a soft fittability, capable of following the stretch of the skin, being of light weight, with a better feeling and ventilation, easily put on to a leg region for easy expansion at wearing, and relatively adjustable to the variation of the size of the lower leg region of a wearer, can be provided.

According to one of the preferable embodiments of the lower leg protection garment of the present invention, the main body comprises a material with a weak straining force and a material with a strong straining force is further superimposed to the surface and/or the underside of the material with a weak straining force to provide a portion with a strong straining force wherein the material with a weak straining force comprises an all ways stretch tricot. Thus, a lower leg protection garment which can be easily produced by only forming a base material of the protection garment main body with a material with a weak straining force, and fixing a material with a strong straining force to the surface and/or the underside of the base material in the necessary region by an appropriate means such as stitching or adhesion without the time consuming operation of alternately seaming a portion with a weak straining force and a portion with a strong straining force, and which further provides a soft fittability, capable of following the stretch of the skin, being of light weight, with a better feeling and ventilation, easily put on to a leg region for easy expansion at wearing, and relatively adjustable to the variation of the size of the lower leg region of a wearer, can be provided.

According to one of the preferable embodiments of the lower leg protection garment of the present invention, a portion with a strong straining force comprises a spandex power net which is a knit fabric much thinner than pile fabric or neoprene used in conventional supporters and can provide a straining force sufficient for a portion with a strong straining force, a lower leg protection garment having a good fittability, being lightweight, without disturbing the movements of the muscle, with a better feeling can be provided. Further, since the material is thin, unlike a thick fabric which may form wrinkles when bending an ankle to compress the joint region with the thickness of the wrinkles to cause problems such as preventing the bending of the joint or causing wearing discomfort, a lower leg protection garment with a good wearing comfort and without disturbing necessary physical movements can be provided.

According to one of the preferable embodiments of the lower leg protection garment of the present invention, a crotch portion is further provided to form a pants-like shape. Such a lower leg protection garment can be easily put on with an easy operation like putting on pants, in the desired position and the appropriate orientation. The risk of the garment sliding down due to the physical movements is reduced by having the waist portion to be secured to the waist, unlike protection garments having the length only to the lower leg region or to the thigh region.

DETAILED DESCRIPTION OF THE INVENTION

Although the lower leg protection garments of the present invention will be explained with reference to Examples and drawings in order to facilitate understanding, the present invention will not be limited to the embodiments of these Examples.

Figure 1:
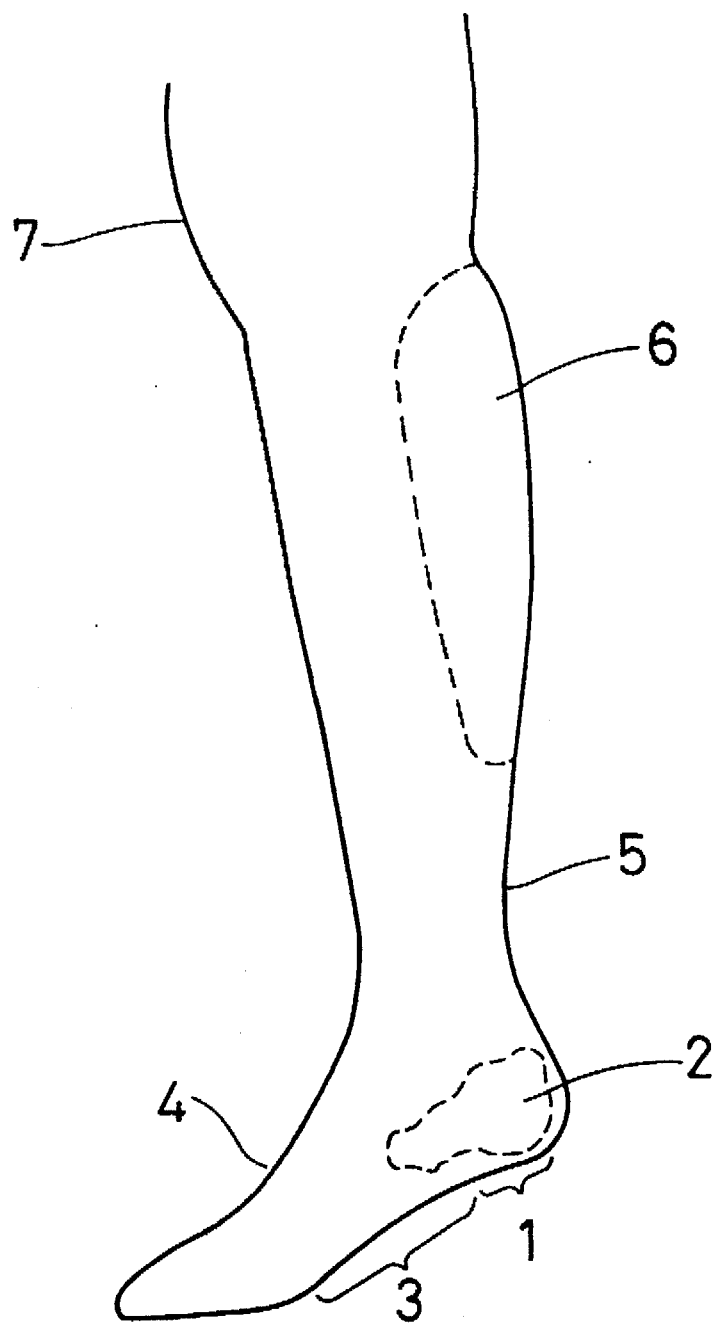
FIG. 1 is a diagram of a lower leg region viewed from the left side.

FIG. 1 is a diagram of the lower leg region viewed from the left side to illustrate names of each portion in the lower leg region to facilitate understanding of the present invention. However, names of commonly known regions such as malleolus, heel, ankle, and crus (region between the knee and foot in the front side of a human body) are not illustrated in FIG. 1. Malleolus medialis is the malleolus of the center side of a human body and malleolus lateralis is the malleolus of the outer side of a human body.

In FIG. 1, numeral 1 denotes tuber calcaneus, 2 heel bone, 3 plantar arch, 4 dorsum pedis or instep, 5 Achilles' tendon and 6 gastrocnemius or calf muscle. Numeral 7 illustrates the position of the knee joint.

Figure 2:
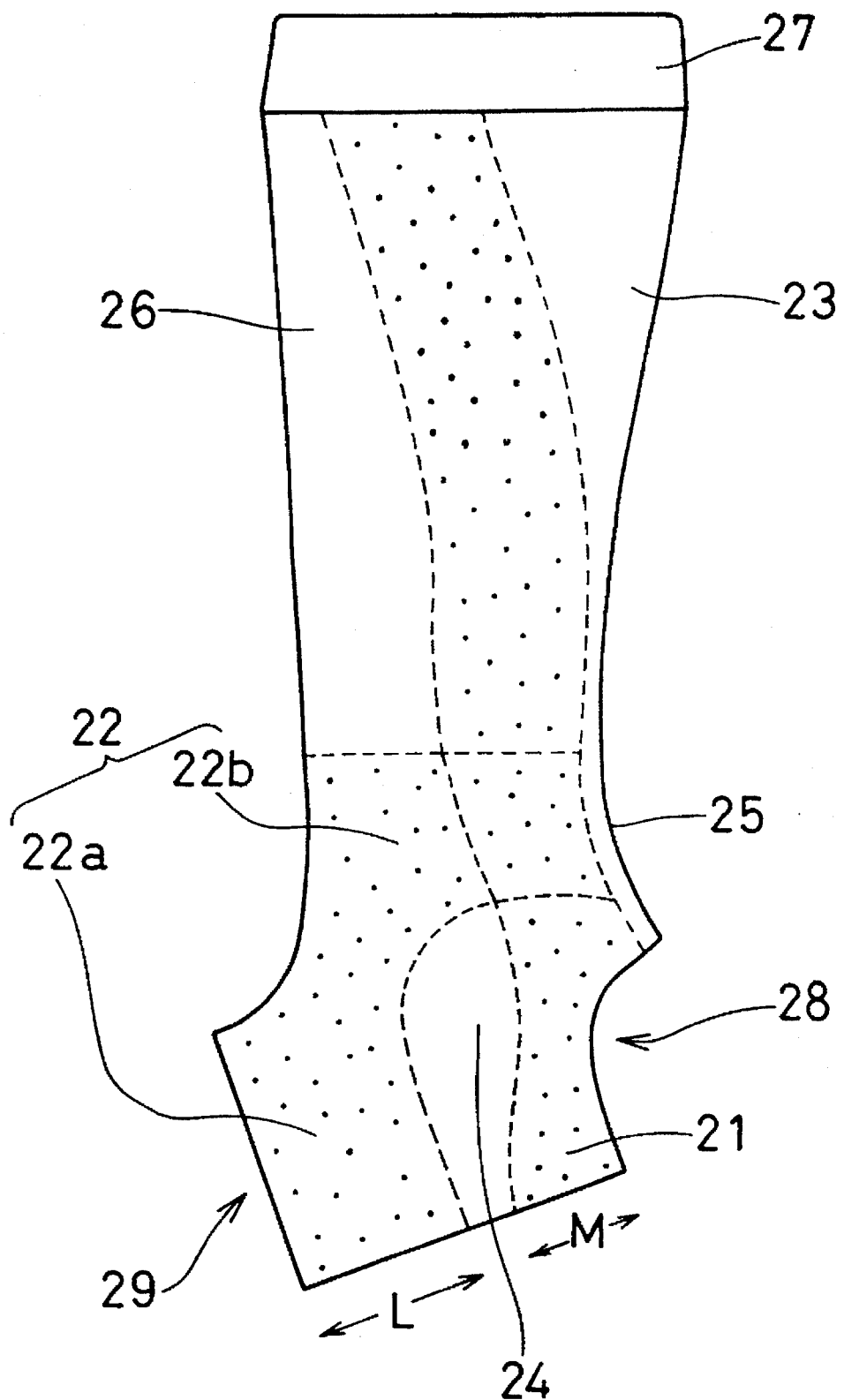
FIG. 2 is a side view of one embodiment of lower leg protection garments of the present invention.
Figure 3:
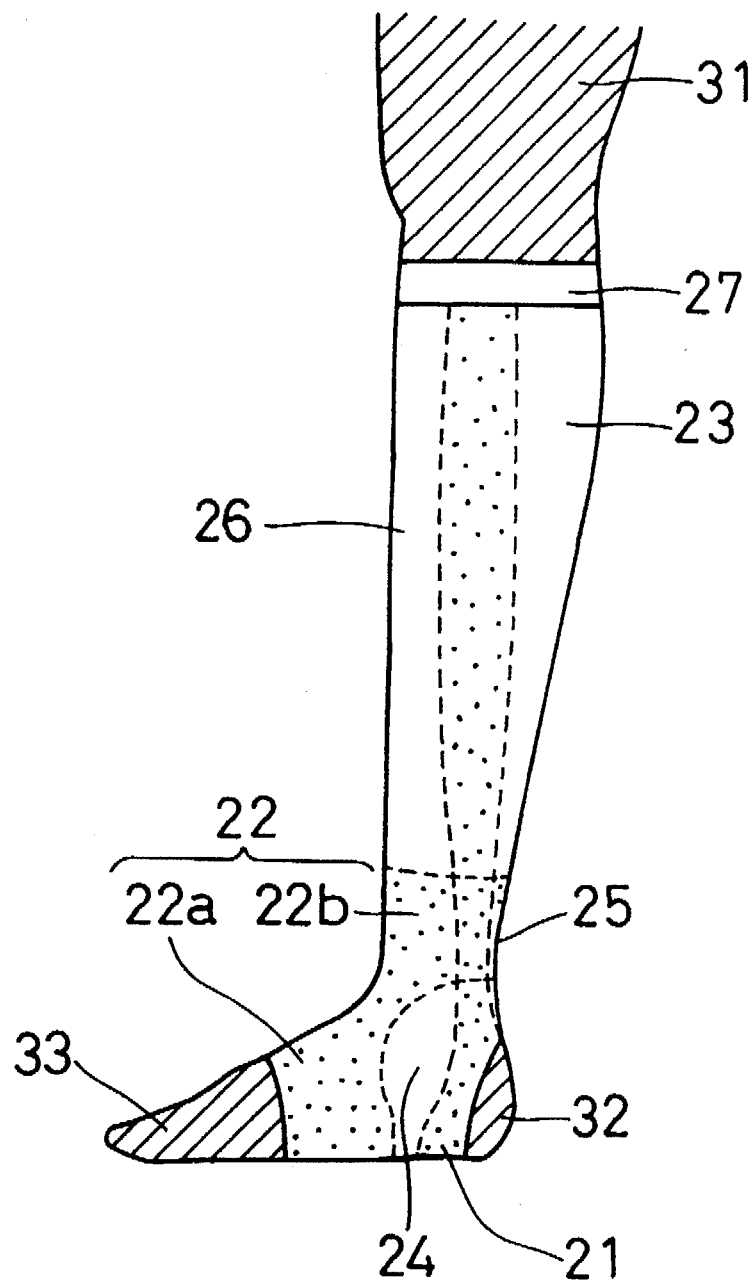
FIG. 3 is a side view of the lower leg protection garment of FIG. 2, illustrated as it would be positioned on a human body viewed from the left side.
Figure 4:
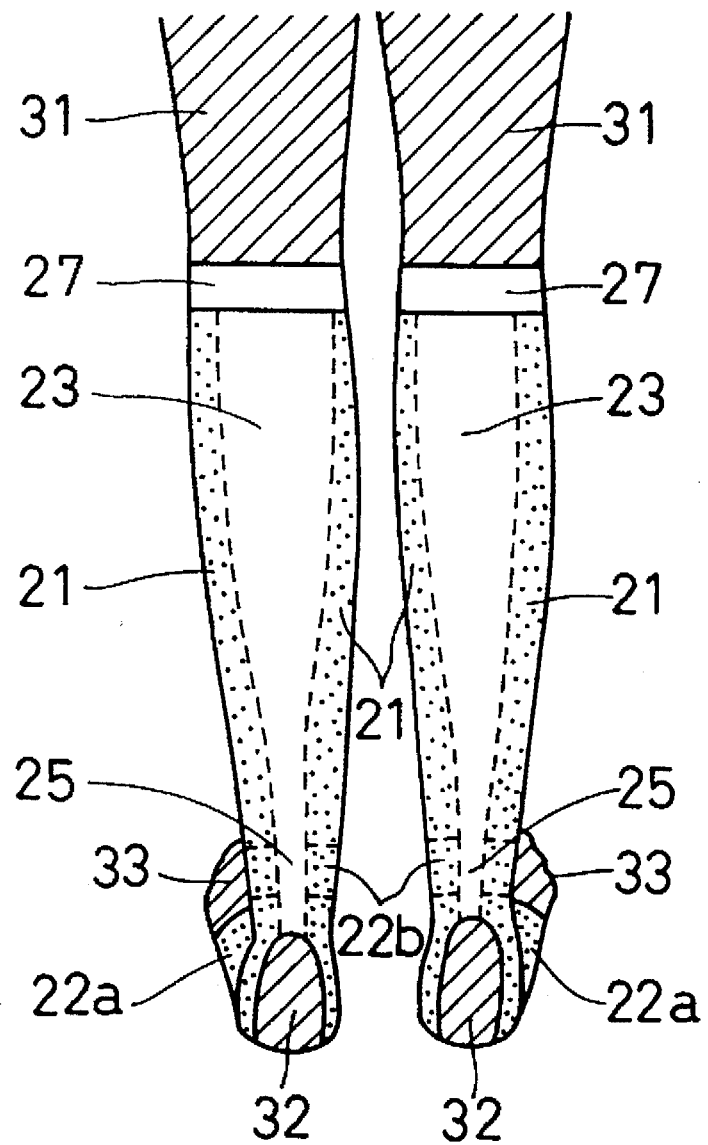
FIG. 4 is a rear view of the lower leg protection garment of FIG. 2, illustrated as it would be positioned on a human body viewed from the back side.
Figure 5:
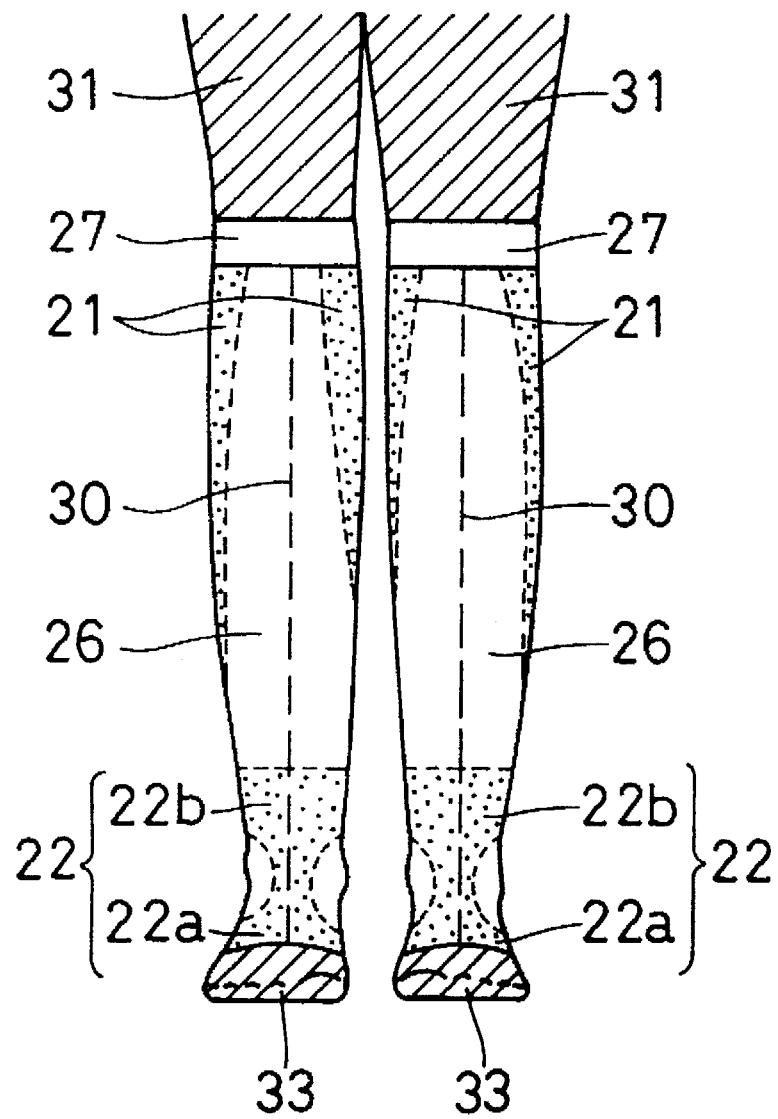
FIG. 5 is a front view of the lower leg protection garment of FIG. 2, illustrated as it would be positioned on a human body viewed from the front side.

FIG. 2 is a side view of one embodiment of lower leg protection garments of the present invention. This is a side view of the lower leg protection garment folded along the center line of the front side and the center line of the back side. FIG. 3 is a side view illustrated as it would be positioned on a human body and viewed from the left side. FIG. 4 is a rear view illustrated as it would be positioned on a human body viewed from the back side. FIG. 5 is a front view illustrated as it would be positioned on a human body and viewed from the front side. FIG. 6 illustrates a development of the material with a weak straining force comprising the lower leg protection garment illustrated in FIGS. 2 to 5. FIG. 7 illustrates a development of the material with a strong straining force comprising the lower leg protection garment illustrated in FIGS. 2 to 5.

The lower leg protection garment illustrated in FIGS. 2 to 5 covers from the sole region to the vicinity of the region just below the knee joint. In this Example, the material of the main body of the lower leg protection garment is formed with a material with a weak straining force in a tube-like shape to cover the region from the vicinity of the region just below the knee joint to the vicinity of the ankle. Further, a portion where a strong straining force is needed is lined with a material with a strong straining force to make a portion with a strong straining force. Therefore a portion not lined with a material with a strong straining force provides a portion with a weak straining force.

The first portion with a strong straining force 21 covers at least a part of the tuber calcaneus (In this case, the portion covers the tuber calcaneus region excluding a part of the back side of the heel to just before the plantar arch: the width M at the sole is 1.5 cm.) across the sole, and extends to the back side of the malleolus medialis and malleolus lateralis to avoid the regions, avoiding the center portion of the Achilles' tendon 25 and extending to the vicinity of the both sides upward and along the slightly outer side of the vicinity of the longitudinal sides of the motor point of gastrocnemius to cover a part of the sides of a lower leg region to reach the upper piece 27 located in the vicinity of the region just below the knee joint. Since the malleolus regions are covered with a material with a weak straining force 24, good wearing comfort is secured by not compressing the malleolus strongly. Although each gastrocnemius has two separate heads, they are treated as one element for convenience herein.

The width of the portion with a strong straining force extending upward along the slightly outer side of the vicinity of the longitudinal sides of the motor point of gastrocnemius to cover a part of the sides of a lower leg region to reach the upper piece 27 located in the vicinity of the region just below the knee joint is preferably about 3 cm or more, more preferably about 4 cm or more, in the narrowest portion in the region in the vicinity of the motor point of gastrocnemius. This permits the straining force to lift up and stabilize the heel to be provided sufficiently. The upper limit of the width is not specifically limited, and all of the portion with a weak straining force at the crus 26 can be replaced with a portion with a strong straining force. In general, it is preferable to determine the upper limit of the width of the above mentioned portion according to the degree of the straining force required by the wearer. However, at least one third of the area of the portion forming the tube-like shape should be formed with a portion with a weak straining force, and if the ratio of the area with the portion with a weak straining force is smaller and the ratio of the area with the portion with a strong straining force is greater, the garment may be too tight for a wearer to expand and wear with ease or wearing comfort may be disturbed by compressing the leg from the periphery too tightly.

Although the upper limit of the area of the portion with a weak straining force is not particularly limited, if the area is too large and a portion with a strong straining force is too small, it becomes difficult to provide sufficient protection. Thus it is preferable to have the above mentioned area be no more than about four fifths of the area of the portion forming the tube-like shape.

The second material with a strong straining force 22 covers at least a part of the plantar arch across the sole (The width L at the sole is 6 cm.) to at least a part of dorsum pedis (The region is numbered 22a.) to form a tube-like shape. Since the plantar arch region can be compressed with the portion with a strong straining force, the function to effectively prevent the inflammation of plantar fascia can be provided and further the material with a strong straining force 22 extends from the dorsum pedis in the ankle direction 22b, further covering the front portion of the ankle to form a tube-like shape. The region of the Achilles' tendon 25 is excluded and covered with the material with a weak straining force 23 later described. Such an arrangement is intended not to disturb the movements of the Achilles' tendon, but when a stronger support to the ankle is desired or the overextension (hyperextension) and tearing of the Achilles' tendon is desired, the material with a strong straining force 22 can be applied to the portion of the Achilles' tendon 25 to form a completed tube shape. Since a tendon such as the Achilles' tendon is comparatively a hard region compared with a motor point of gastrocnemius, even if the region is covered with a portion with a strong straining force, it may not cause wearing discomfort. A portion with a weak straining force 26 covers crus in this Example to further facilitate easy expansion to enable easy wearing. The portion with a weak straining force 23 covers a region from the motor point of gastrocnemius to the Achilles' tendon 25 in order not to disturb the movements including contraction of gastrocnemius, which is the most projecting muscle in the lower leg region, and not to allow a portion with a strong straining force to cut into the muscle by locating it on the soft motor point of gastrocnemius, nor to cause a blood circulation disorder. In this Example, as mentioned before, the center portion of the Achilles' tendon 25 is covered with a portion with a weak straining force 23. Numeral 27 is a circular upper piece to prevent the sliding down of the garment. The material of the upper piece is not particularly limited and any material can be used optionally as long as the purpose of the present invention is achieved. For example, the same material as the portion with a weak straining force folded in two can be used to generate a straining force of a medium degree, or a material with a medium straining force, which is stronger than straining force of the portion with a weak straining force, folded in two can be used. As long as the straining force of the portion is not too strong in order not to cause a blood circulation disorder, any material can be optionally applied. Numeral 28 denotes a hole through which the heel protrudes and 29 a hole through which the vicinity of the toe region protrudes. The width at the sole of the first portion with a strong straining force to cover at least a part of tuber calcaneus across sole is not particularly limited but preferably 1 cm or more. The upper limit of the width is not particularly limited and the entire region of the sole can be covered with a portion with a strong straining force.

In FIGS. 3 to 5, numeral 31 denotes the thigh region of a leg of a human body, 32 the heel of a human body, 33 the region in the vicinity of the toe of a foot of a human body. In FIG. 5, numeral 30 denotes the front seam line. The heel region 32 or the region in the vicinity of the toe of a foot 33 may be covered with a portion with a weak straining force or a portion with a strong straining force to form a sock-like shape. But since the garment has both a portion with a weak straining force and a portion with a strong straining force, unlike mere socks, the production process becomes complicated if it is formed to have a sock-like shape, and thus the embodiment illustrated in the figures can be produced much more easily.

Figure 6A:
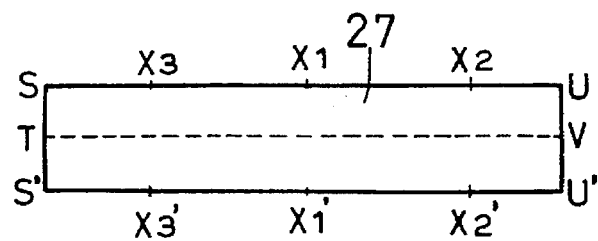
FIGS. 6(a)–6(c) are a development of the material with a weak straining force used in the lower leg protection garment illustrated in FIGS. 2 to 5.
Figure 6B:
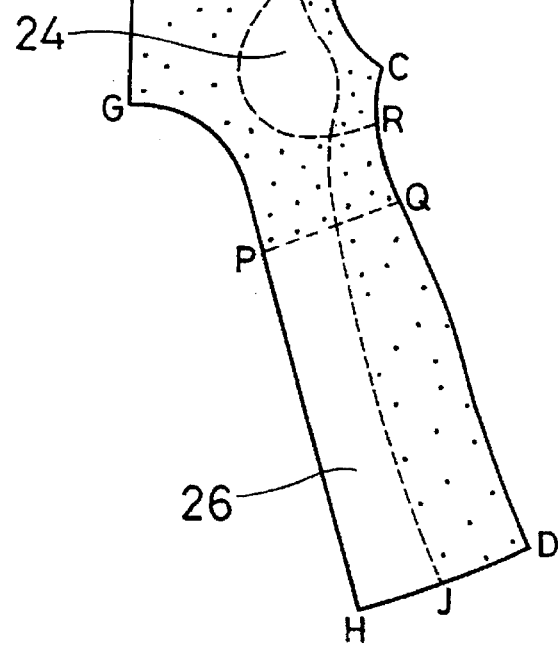
Figure 6C:
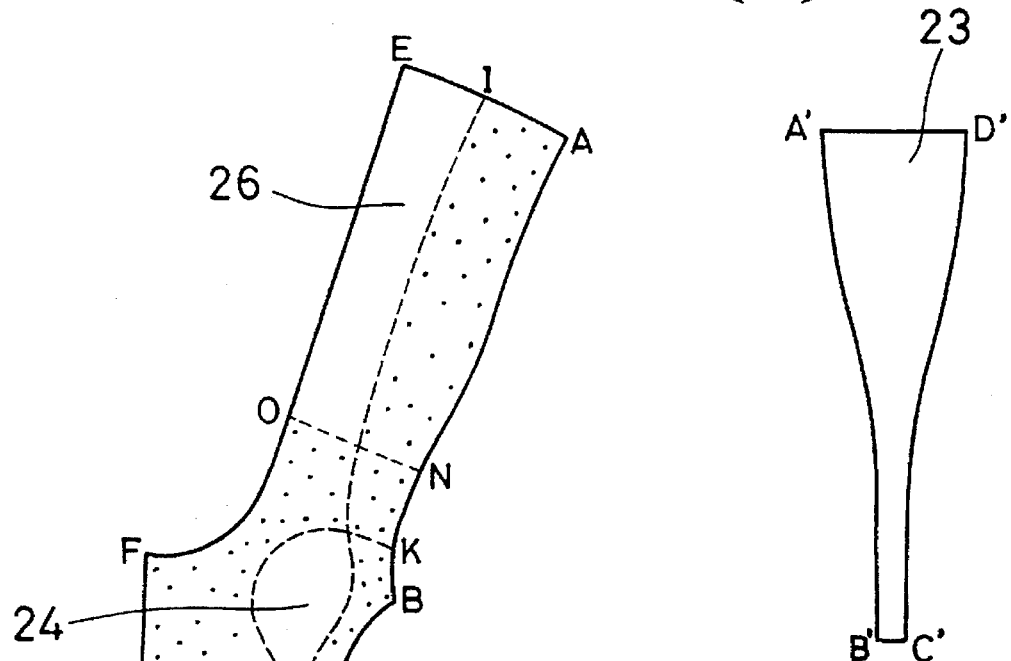
Figure 7A:
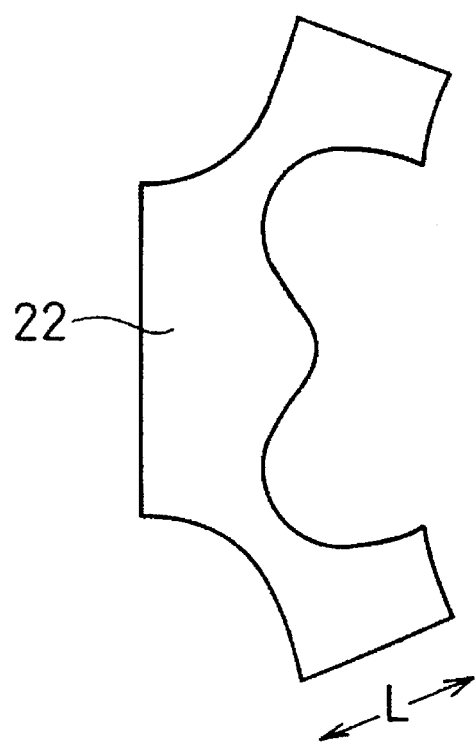
FIGS. 7(a) and 7(b) are a development of the material with a strong straining force used in the lower leg protection garment illustrated in FIGS. 2 to 5.
Figure 7B:
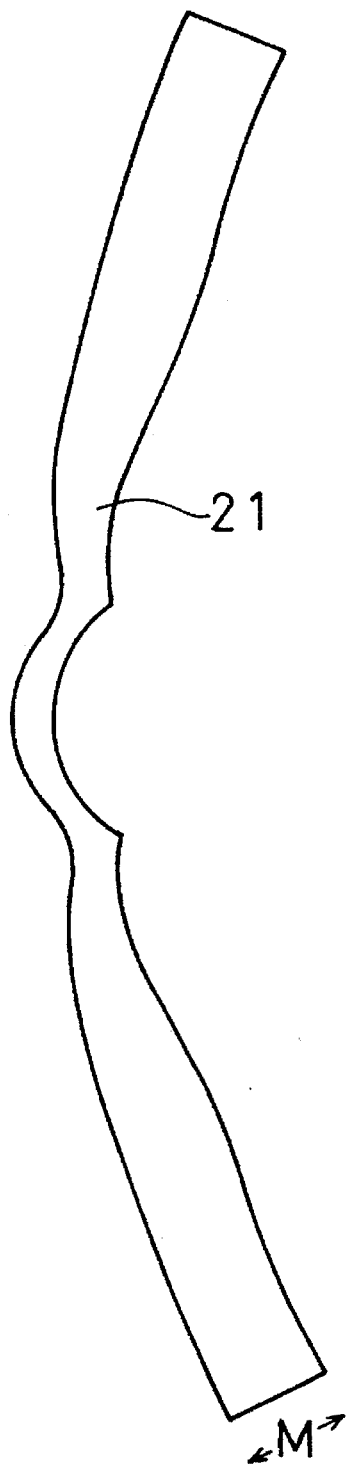

The development of the material with a weak straining force used in the lower leg protection garment described in FIG. 6 will be explained. FIG. 6(a) is a development of the upper piece 27, FIG. 6(b) is a development of the material with a weak straining force to cover the main regions in front, sole, and both sides of the lower leg, and FIG. 6(c) is a development of the material with a weak straining force 23 covering from the motor point of gastrocnemius to the Achilles' tendon 25. The line A-B of the material with a weak straining force in FIG. 6(b) and the line A'-B' of the material with a weak straining force 23 in FIG. 6 (c) are stitched together, the line C-D of the material with a weak straining force in FIG. 6(b) and the line C'-D' of the material with a weak straining force 23 in FIG. 6(c) are stitched together, and further the line E-F and the line H-G are stitched (The stitch line is the front side seam line 30 in FIG. 5.) to form a garment with a tube-like shape. The development of the upper piece 27 in FIG. 6(a) is folded in two along the chained line T-V to superimpose the line S-U to the line S'-U', the line $X_1'$-$X_2'$ ($X_1$-$X_2$) and the line E-A are stitched, the line $X_2'$-U' ($X_2$-U) and the line A'-W are stitched, the line $X_1'$-$X_3'$ ($X_1$-$X_3$) and the line H-D are stitched, the line $X_3'$-S' ($X_3$-S) and the line D'-W are stitched, and further the line V-U' (V-U) and the line T-S' (T-S) are stitched to complete the outline. The portion surrounded by the line A-B-C-D-J-Y-I-A in FIG. 6(b) the portion lined with the first material with a strong straining force 21 from the underside and the portion surrounded by the line Z-K-N-O-F-G-P-Q-R-Z is lined with the second material with strong straining force 22 from the underside. FIG. 7(a) is a development of the second material with a strong straining force 22 and FIG. 7(b) is a development of the first material with a strong straining force 21. These materials with a strong straining force 21, 22 are superimposed to the specified portions illustrated in the development of FIG. 6(b) as described above by means of such as stitching in advance, and then the portions would be stitched to each other as mentioned in the explanation of FIG. 6 to complete the lower leg protection garment of this embodiment.

In this embodiment an all ways stretch tricot comprising 80% of polyester fiber and 20% of polyurethane fiber was used as the material with a weak straining force and a spandex power net comprising 80% of nylon fiber and 20% of polyurethane fiber was used as the material with a strong straining force. The straining force of the portion with a weak straining force formed with only the material with a weak straining force was 63 gf, and the straining force of the portion with a strong straining force formed with the material with a strong straining force of spandex power net superimposed to the material with a weak straining force was 254 gf at the side portions of gastrocnemius, and 213 gf at each sole. Approximately three fifths of the area having a tube-like shape was formed with the portion with a weak straining force.

Since the obtained lower leg protection garment stabilizes the ankle by strongly lifting up the heel with the portion with a strong straining force 21 to reduce the chances of inversion or eversion of the ankle, a lower leg protection garment which stabilizes the ankle even in a twisting or bending motion, providing ankle sprain protection, has good wearing comfort, has good ventilation without stuffiness, has good fittability, has a light weight, without disturbing movements of muscles, with good feeling, is worn easily to the proper position by anybody without the need of skill, without susceptibility of causing blood circulation disorder or nervous disorder, can be provided. Further, since the motor point of gastrocnemius is covered with the portion with a weak straining force in order not to prevent movements including contraction of gastrocnemius, which is one of the important muscles in the lower leg region, the central region of the Achilles' tendon is covered with the portion with a weak straining force in order not to disturb movements of Achilles' tendon and the portion with a strong straining force covers from at least a part of the plantar arch across the sole to at least a part of the dorsum pedis to form a tube-like shape with the width L at the sole of 6 cm (more than 3 cm) further extending to the ankle at the front side to cover the front side of the ankle to form a tube-like shape around the ankle excluding the central region of the Achilles' tendon, a lower leg protection garment which effectively prevents the inflammation of plantar fascia to which a flat-footed person is susceptible, capable of holding the ankle firmly, with the reinforced sprain protection function, can be provided.

Although an embodiment having the lower leg protection garment main body formed with a material with a weak straining force having a material with a strong straining force superimposed to the underside of the material with a weak straining force to form a portion with a weak straining force and a portion with a strong straining force respectively is described in the above mentioned Example, a lower leg protection garment of the present invention may be formed by preparing a portion with a weak straining force and a portion with a strong straining force with an appropriate material and seaming them alternately at certain positions.

Although an embodiment of superimposing a material with a strong straining force to a material with a weak straining force is illustrated in the above mentioned Example as an example of means to form a portion with a strong straining force such as superimposing a different material to certain portions to the material with a weak straining force or applying other treatments to increase the straining force, the invention is not limited thereto and other methods such as forming a portion with a strong straining force by superimposing a material with a strong straining force and/or a material with a weak straining force to the surface and/or the rear surface of the specified portions of the material with a weak straining force. That is, the material to superimpose is not limited to a material with a strong straining force but a material with a weak straining force can be used to superimpose to reinforce the straining force in the superimposed portion to make the straining force of the superimposed portion greater than other portion not superimposed to form a portion with a strong straining force. Further, by adhering a film or net of an elastic resin, coating an elastic resin solution or emulsion, or applying resin treatment to the specified portions of the lower leg protection garment main body with a material with a weak straining force, a portion with a strong straining force can be formed as well. When the material is made by knitting, a portion with a strong straining force and a portion with a weak straining force may be formed by changing the knit structure or using different materials, such as different kinds of the fiber threads.

The thickness of the material for a material with a strong straining force and a material with a weak straining force is preferably between 0.3 to 0.8 mm, namely the thickness of a common woven fabric or knit fabric, since this will provide thinness, lightweight, good fittability, good ventilation without disturbing movements, nor ruining silhouette by reflecting the garment shape to the outer wear. Elastic woven fabrics or knitted fabrics are preferable and examples include knit fabrics such as plain fabrics, rib stitch fabrics, fabrics knitted with raschel knitter and tricot. Since materials of the same knit structure may have different straining force by changing the kind or thickness of the thread or the ratio of the elastic fiber content, a portion with a strong straining force and a portion with a weak straining force may be prepared by such means. It is preferable that a material with a strong straining force and a material with a weak straining force have elasticity in both horizontal and longitudinal orientations. In particular, a spandex power net, a kind of raschel knit fabrics is preferable for a material with a strong straining force and an all ways stretch tricot among tricot knittings are preferable as a material with a weak straining force.

The techniques heretofore mentioned are not limited to this Example but can be applied to other Examples or other embodiments.

Concerning the straining force of a portion with a strong straining force and a portion with a weak straining force, the straining force of a portion with a strong straining force is preferably 100 to 400 gf, more preferably 150 gf to 300 gf. The straining force of a portion with a weak straining force is preferably 30 to 250 gf, more preferably 30 to 150 gf and weaker than that of the portion with a strong straining force used. When straining force is varied in a protection garment in three stages or more, the portion having the weakest straining force is a portion with a weak straining force and other portions having stronger straining force are portions with a strong straining force. Besides, it is preferable that the straining force of a portion with a strong straining force is greater than that of a portion with a weak straining force by 1.5 times or more.

As the concrete method to measure a straining force, Constant-Rate of Specimen-Extension (CRE) type tensile tester ("AUTOGRAPH" AG-500D made by Shimadzu Corporation) is used to conduct stretch and recovery for three times at a tension speed of 300±20 mm/min by 80% of the length of the specimen length (the clamping distance) and the load of the time of 50% recovery of the third stretch is recorded as the straining force. The preferable size of the specimen is 2.5 cm in width and 10 cm in length but in case it is impossible to cut out the specimen of that size from a lower leg protection garment, the size of specimen may be smaller. However, as the size of the specimen becomes smaller, the measurement error becomes greater, and thus it is preferable to pick up as large a specimen as possible for measuring. However, in case a plurality of specimens are taken from a garment subject to measuring, specimens having the same size and same shape with respect to the stretching direction of the specimen need to be collected for measurement and comparison. In the tube-like portion of the garment, measuring is conducted with the garment width to be the stretching direction. As for the sole portion, the direction across the sole is to be placed as the stretching direction. The straining force of the portion with a strong straining force and the portion with a weak straining force may vary naturally but even the portions with a strong straining force using the same material may have a slightly different value depending upon the measuring positions.

Figure 8:
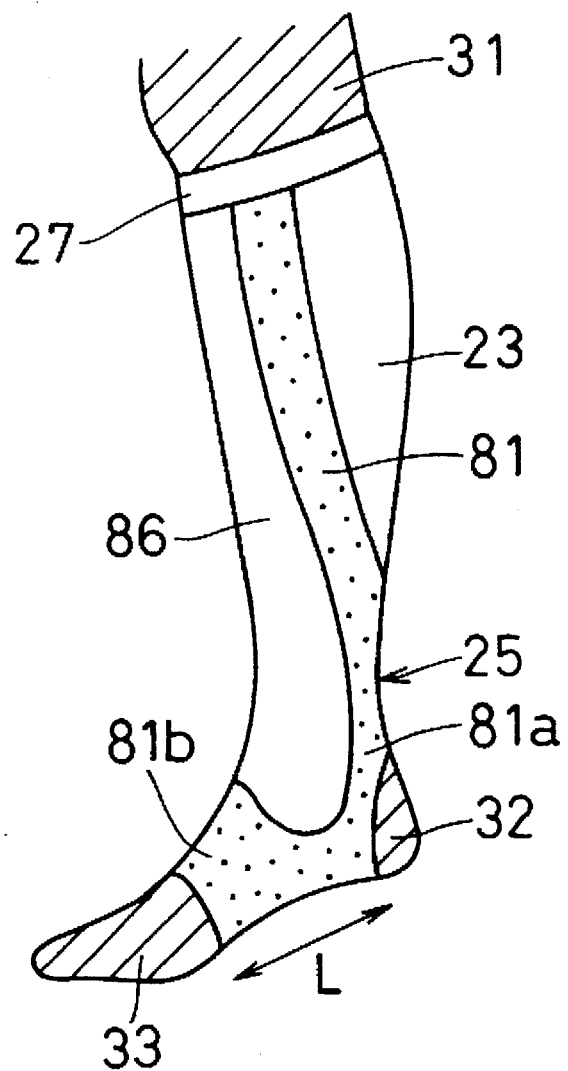
FIG. 8 is a perspective view of another embodiment of lower leg protection garments of the present invention, illustrated it would be positioned on the left leg of a human body viewed from the left side.

FIG. 8 is a perspective view of another Example of the lower leg protection garment of the present invention viewed from the left side, illustrated as it would be positioned on the left leg of a wearer.

In FIG. 8, since the portions the same as those of FIGS. 2 to 7 are applied with the same numerals, detailed explanation is omitted. Like the lower leg protection garment of the embodiment illustrated in FIGS. 2 to 7, the lower leg protection garment of FIG. 8 comprises the main body formed with a material with a weak straining force and the portions at which a strong straining force are needed are lined with a material with a strong straining force by stitching. Therefore a portion to which a material with a strong straining force is not lined is the portion with a weak straining force.

The major difference between the lower lee protection garment of FIG. 8 and the lower leg protection garment of FIGS. 2 to 7 is the shape and position of the portion with a strong straining force to which a material with a strong straining force 81 is applied. In the Example of FIGS. 2 to 7, the portion with a strong straining force is formed with the first material with a strong straining force 21 and the second material with a strong straining force 22 whereas in the lower lee protection garment of FIG. 8, the portion with a strong straining force is formed with a material with a strong straining force 81 providing the unified function of the portions 21, 22, covering from the tuber calcaneus excluding a rear part of heel to the plantar arch across the sole (width at the sole L: 8 cm), not having a portion 22b extending to the ankle covering the front part of ankle forming a tube-like shape. The portion applied on the Achilles' tendon 25 comprises only a material with a weak straining force 23 without having a material with a strong straining force 81. Although the feature is not apparent from the FIG. 8 since it doesn't have a rear view, the back side of the garment is virtually the same as FIG. 4. The portion with a weak straining force 86 covers from the crus to a part of the ankle and the malleolus region, and the opposite side has the approximately the same structure.

That is, the material with a strong straining force 81 covers from the tuber calcaneus to the plantar arch across the sole, extending to two directions. The one 81a extends to the back side of malleolus medialis and malleolus lateralis, avoiding these medialis regions, avoiding the center portion of the Achilles' tendon 25 and extending to the vicinity of the both sides upward along the slightly outer side of the vicinity of longitudinal sides of the motor point of gastrocnemius to cover a part of the sides of the lower leg region to reach the upper piece 27 located in the vicinity of the region just below the knee joint. The other one 81b covers the plantar arch across the sole to at least a part of dorsum pedis to form a tube-like shape. In this Example, an all ways stretch tricot comprising 80% of polyester fiber and 20% of polyurethane fiber was used as the material with a weak straining force and a spandex power net comprising 80% of nylon fiber and 20% of polyurethane fiber was used as the material with a strong straining force. The straining force of the portion with a weak straining force formed with only a material with a weak straining force was 63 gf, and the straining force of the portion with a strong straining force formed by superimposing a spandex power net as the material with a strong straining force from the rear surface of the above mentioned portion with a weak straining force of the all ways stretch tricot was 254 gf at the sides of gastrocnemius and 213 gf at the sole. Approximately two thirds of the area in the portion with a tube-like shape was formed with a portion with a weak straining force.

Since the lower leg protection garment of FIG. 8 stabilizes the ankle by strongly lifting up the heel with the portion 81a of the portion with a strong straining force 81 to prevent inversion or eversion of the ankle, a lower leg protection garment which stabilizes the ankle even in twisting or bending motion, provides ankle sprain protection, with good wearing comfort, provides good ventilation without stuffiness, good fittability, is lightweight, without disturbing movements of muscles, with good feeling, is worn easily on the proper position by anybody without the need of skill, without susceptibility of causing blood circulation disorder or nervous disorder can be provided. Further, since the motor point of gastrocnemius is covered with the material with a weak straining force not to prevent movements including contraction of gastrocnemius, which is one of important muscles in the lower leg region, the central region of the Achilles' tendon is covered with the material with a weak straining force not to disturb movements of Achilles' tendon and the portion with a strong straining force covers from at least a part of the plantar arch across the sole to at least a part of the dorsum pedis to form a tube-like shape with the width L at the sole of 8 cm (more than 3 cm), a lower leg protection garment which can effectively prevent the inflammation of plantar fascia to which a flat-footed person is susceptible, can be provided. The lower leg protection garment of FIG. 8 protects against the inversion and eversion of the ankle region which is the cause of sprain as the Example of FIGS. 2 to 7, but it differs from the embodiment of FIGS. 2 to 7 in the point that it is designed not to disturb the upward and downward movements of the ankle. In FIG. 8, the heel portion 32 and the toe portion 33 may be covered with a portion with a weak straining force or a portion with a strong straining force to form a sock-like shape, but it would complicate the production process as mentioned before.

Figure 9:
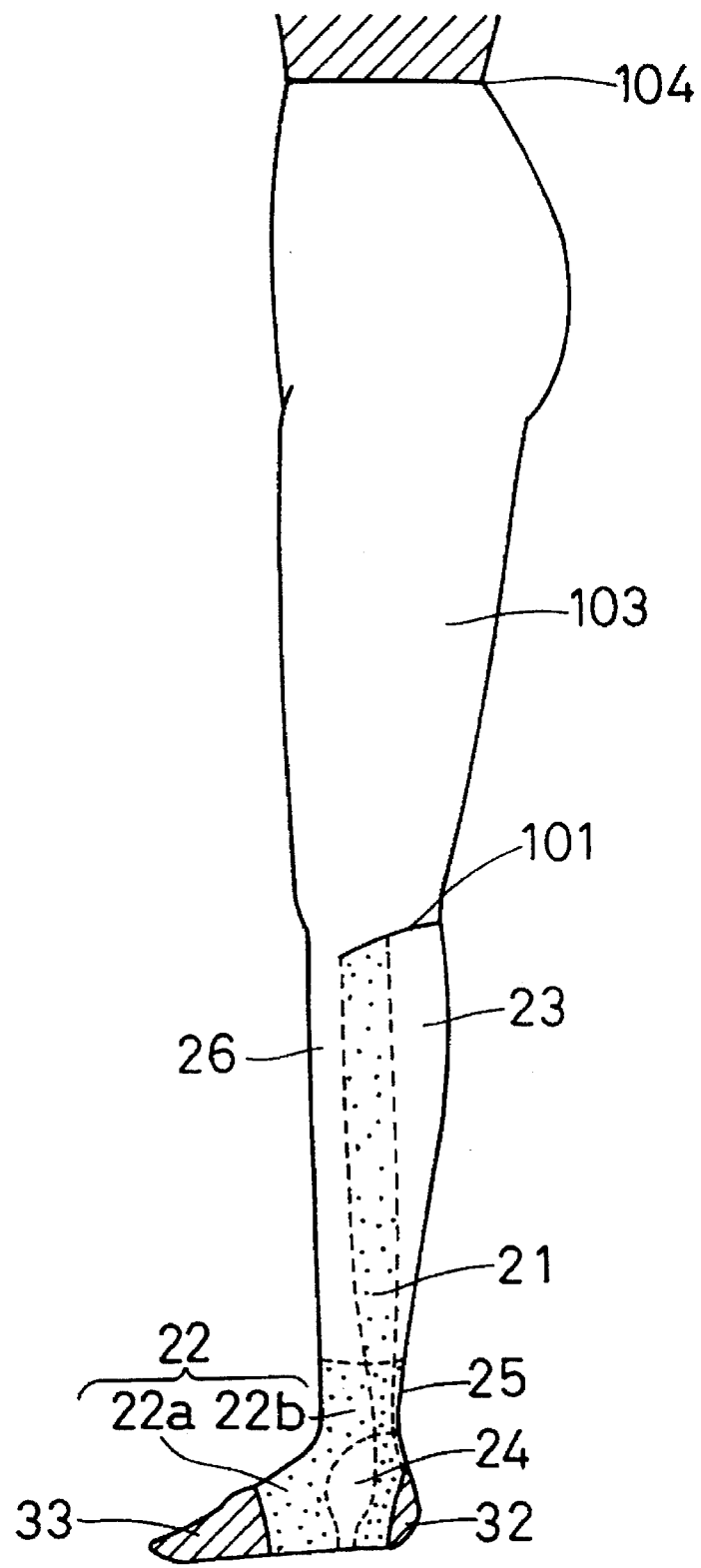
FIG. 9 is a side view of an embodiment of lower leg protection garments of the present invention having a crotch portion to form a pants-like shape, illustrated as it would be positioned on a human body viewed from the left side.
Figure 10:
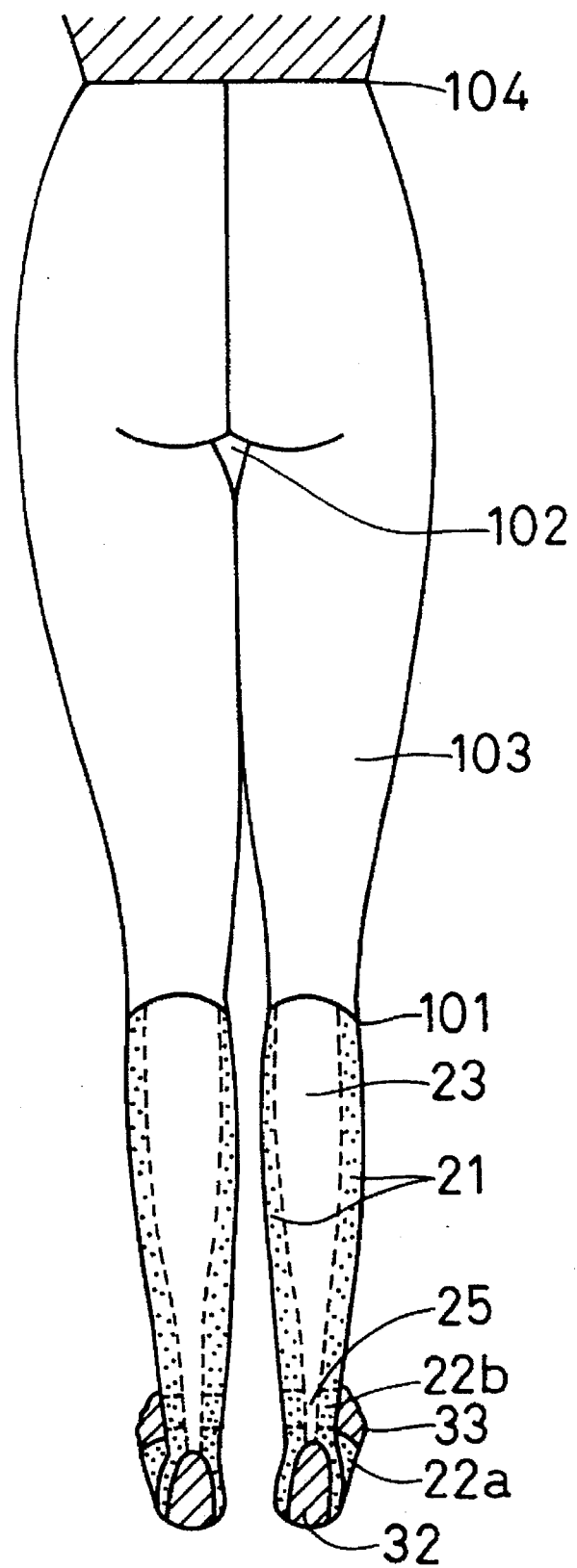
FIG. 10 is a rear view of the lower leg protection garment of FIG. 9, illustrated as it would be positioned on a human body viewed from the back side.
Figure 11:
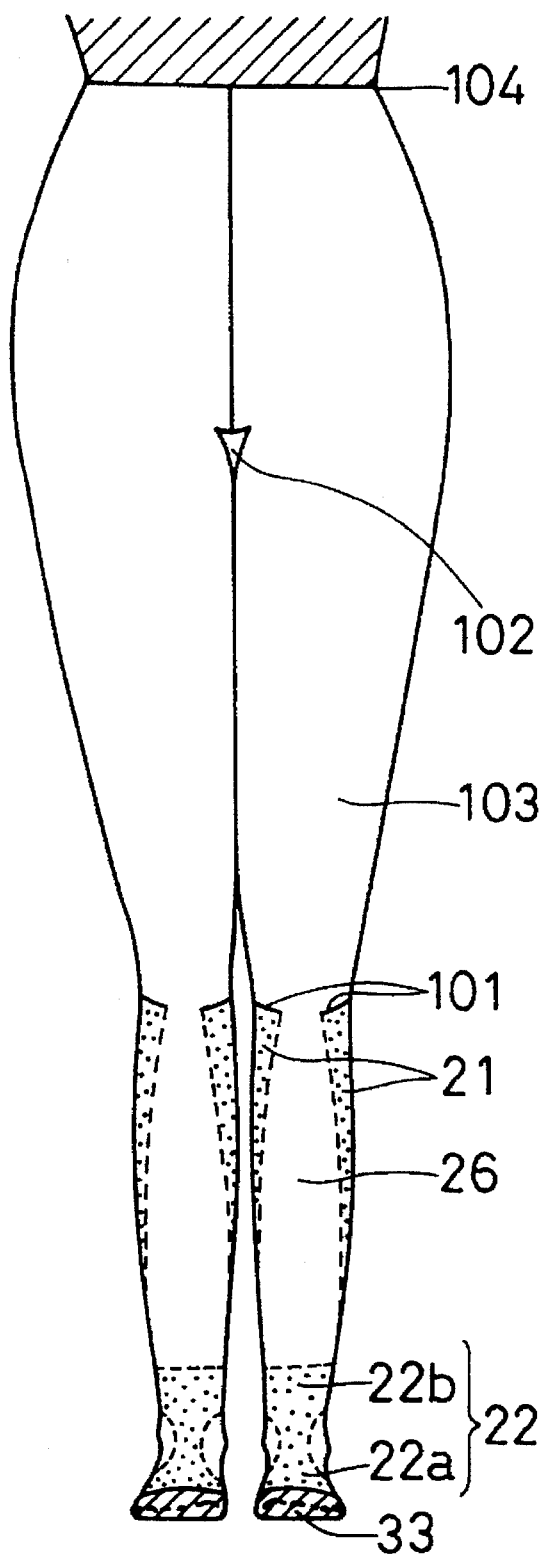
FIG. 11 is a front view of the lower leg protection garment of FIG. 9, illustrated as it would be positioned on a human body viewed from the front side.

FIGS. 9 to 11 illustrate an embodiment of lower leg protection garment having a crotch portion to form a pants-like shape. FIG. 9 is a side view of the garment illustrated as it would be positioned on a human body and viewed from the left side. FIG. 10 is a rear view of the garment illustrated as it would be positioned on a human body and viewed from the back side. FIG. 11 is a front view of the garment illustrated as it would be positioned on a human body and viewed from the front side.

Since most structures in the lower leg region are the same as the lower leg protection garment of FIGS. 2 to 5 (hereinafter abbreviated Example 1), the same numerals are applied to the same portions and further explanation is omitted. The protection garment of FIGS. 9 to 11 does not have an upper piece 27 of the previous first embodiment, and instead it extends upward to the waist region 104 to form the portion from the knee joint and above 103 with a crotch portion 102 to form a pants-like protection garment. That is, the main body of the lower leg protection garment of this Example comprises a material with a weak straining force from the sole portion to the waist portion and a material with a strong straining force is lined by stitching to the portions where a strong straining force is desired to form a portion with a strong straining force. Therefore portions without a lining of the material with a strong straining force is a portion with a weak straining force. Since the portion lined with a material with a strong straining force is virtually the same as the embodiment of FIGS. 2 to 5, further explanation is omitted. In FIGS. 9 to 11, numeral 101 denotes a seam line from the back side of the knee joint to the front side of the region just below the knee joint seamed with a dart. Although stitching with the dart enables this portion to closely fit to the human body, the dart is optional and does not always have to be formed. Although an embodiment with the portion of the knee joint and above 103 seamed with the portion covering the lower leg region therebelow to form a pants-like shape is illustrated, other embodiments such as the one forming a pants-like shape integrally without seaming at the portion of seaming line 101, and further in that case a portion corresponding with a part of the seaming line 101, for example, from the back side of the knee to the sides of the knee can be formed with a dart to enable the portion to closely fit to the human body. Since the above mentioned embodiment of seaming at the region just below the knee joint enables the use of different materials for the portion including the knee joint and above 103 and the portion applied to the lower leg region therebelow according to the required properties, it allows the broader choice of materials compared with embodiments forming the upper portion and the lower portion integrally, and eliminates the problem in producing the upper portion and the lower portion integrally. Since the production of the lower leg portion is comparatively complicated and having the upper portion 103 would be disadvantageous with respect to production operativity, it is preferable because a lower leg protection garment without production problems including excessive time consumption can be provided. It is easily understood that the portion below the knee joint can be not only the embodiment illustrated in FIGS. 9 to 11 but other embodiments such as the one illustrated in FIG. 8.

In the embodiment of FIGS. 9 to 11, the portion of knee joint and above 103 is formed with a material with a weak straining force. An all ways stretch tricot of 80% of polyester fiber and 20% of polyurethane fiber was used as the material with the weak straining force in this embodiment. And as the material with a strong straining force, a spandex power net of 80% of nylon fiber and 20% of polyurethane fiber was used. The straining force of the portion with a weak straining force formed only with the material with a weak straining force was 63 gf, and the straining force of a portion with a strong straining force formed by superimposing a spandex power net as the material with a strong straining force to the rear surface of the material with a weak straining force of the above mentioned all ways stretch tricot was 254 gf at the side portions of gastrocnemius and 213 gf at each sole. Approximately three fifths of the area comprising the tube-like shape in the region below the knee joint is formed with a portion with a weak straining force.

By forming a pants-like lower leg protection garment, the protection garment has the following advantages in addition to those explained in the Example of FIGS. 2 to 7, such as easiness in putting on with an easy operation like putting on pants to the proper position and appropriate orientation, and prevention of sliding down superior to that of protection garments having the length only to the lower leg region by being secured to the waist region.

Moreover, a lower leg protection garment further comprising an appropriate bone to firmly support the heel or the ankle can be provided in this invention. When such a bone is provided, it is mounted to the surface and/or the underside of the lower leg protection garment of the present invention. In general, it is mounted to the underside of the lower leg protection garment, i.e. the body-facing side.

The position to mount a bone is preferably a portion covering at least a part of heel bone and/or a portion at least in the vicinity of the ankle, avoiding the malleolus medialis and malleolus lateralis regions in the lower leg region. Since illustrating the position to mount a bone on a figure of a lower leg protection garment of the present invention would complicate the figure, the approximate positions are described in diagrams of human lower leg regions FIG. 12 to FIG. 15. However, it would be easily understood that the positions may change slightly according to embodiments of lower leg protection garments of the present invention.

Figure 12:
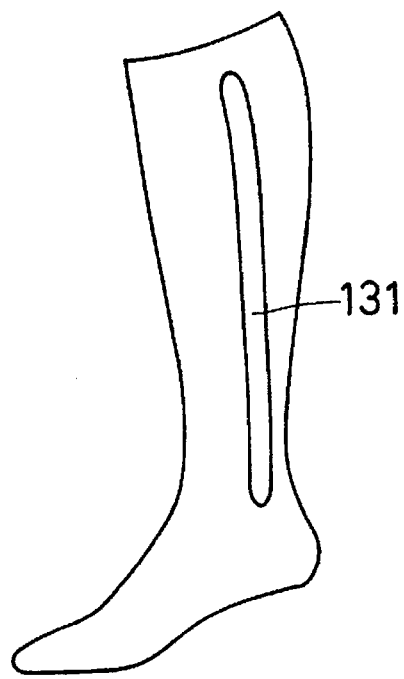
FIG. 12 is a diagram to illustrate the position to attach a bone of one embodiment of the present invention.

FIG. 12 is a diagram of one embodiment illustrating the position to mount a bone. The bone 131 extends from the back side of the malleolus in the upward direction, covering the vicinity of the outer side of the motor point of gastrocnemius longitudinally to the region a little lower than the knee joint. In case of using a bone, it is preferable similarly to have another bone at the opposite side with respect to reinforcement of the prevention effect of inversion or eversion of the ankle, but a bone can be provided only in one side of a leg. It can be determined according to the purpose or the desired degree of supporting the leg. The same thing can be applied to the following embodiments.

Figure 13:
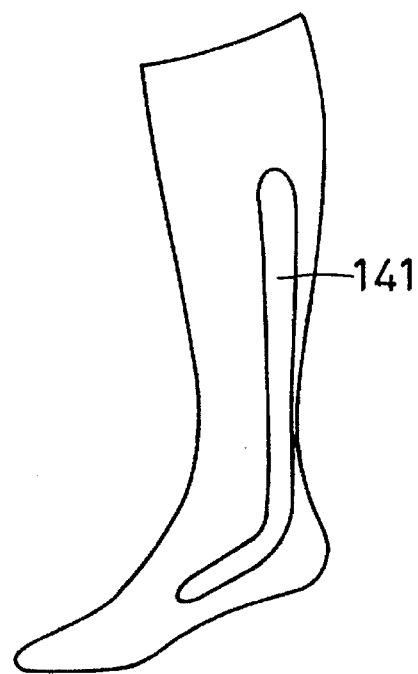
FIG. 13 is a diagram to illustrate the position to attach a bone of another embodiment of the present invention.

FIG. 13 is a diagram of another embodiment illustrating the position to mount a bone. The bone 141 extends from a portion lower than the malleolus, to the back side of the malleolus and upward along the side of the lower leg region slightly to the back. In this embodiment, the protection against inversion and eversion, twisting and bending of the ankle and ankle sprain are reinforced by further supporting the ankle from the sides slightly to the back to firmly fix the region.

Figure 14:
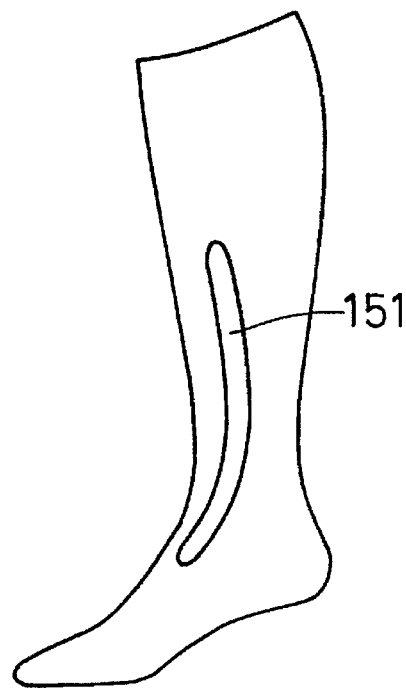
FIG. 14 is a diagram to illustrate the position to attach a bone of a further different embodiment of the present invention.

FIG. 14 is a diagram of a further different embodiment illustrating the position to mount a bone. The bone 151 extends from a portion of dorsum pedis to the upper part of the malleolus along the side of the lower leg region upward slightly to the crus region. In this embodiment, the protection against inversion and eversion, twisting and bending and ankle sprain are reinforced by further supporting the ankle from the side slightly to the front region to firmly fix the region.

Figure 15:
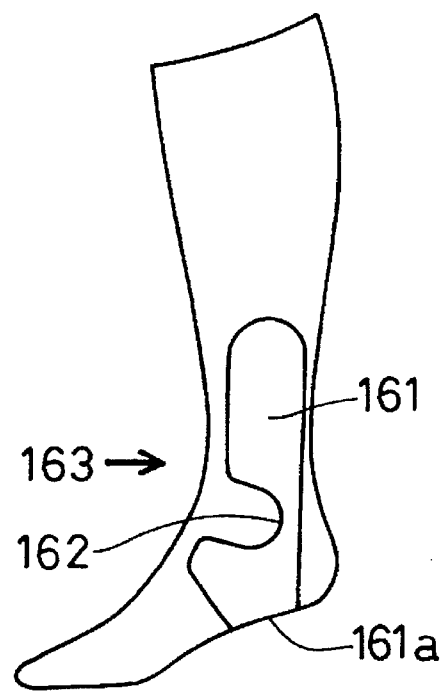
FIG. 15 is a diagram to illustrate the position to attach a bone of another embodiment of the present invention.
Figure 16:
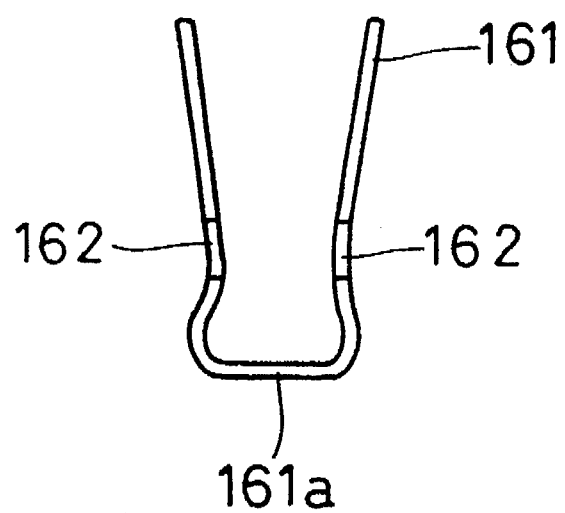
FIG. 16 is a front view of the bone of FIG. 15, viewed from the position of the arrow 163.

FIG. 15 is a diagram of a further different embodiment illustrating the position to mount a bone. The bone 161 having a wider length plate-like shape extends from the upper direction downward avoiding the malleolus region to form the U-shaped notch portion 162 from the upper direction further to cover a part of the tuber calcaneus and a part of the plantar arch across the sole extending similarly to the other side to the similar portion as the outer side of the leg. The portion of the bone covering the sole region is numbered 161a. FIG. 16 is a front view of the bone viewed from the position of the arrow 163 illustrated in FIG. 15. Since the bone is provided with the U-shaped notch portions 162 avoiding the malleolus medialis and malleolus lateralis so as not to cause discomfort by compressing the projection of the malleolus while firmly protecting the ankle with the wider plate-like shape and stabilizing the heel by lifting up with the portion covering a part of the tuber calcaneus and a part of heel across the sole, the prevention of the inversion and eversion, and prevention of twisting and bending of the ankle are further reinforced to prevent the ankle sprain in this embodiment. Further, the lower leg protection garment with the bone of the present invention allows sports activities for the wearer.

The embodiments of the bone are not specifically limited but a bone of plastic is preferable for being lightweight. And the thickness of bones is not specifically limited but, in general, ones with 0.5 to 3 mm thickness are preferably used.

The plastic material for the bone is not specifically limited but amorphous resins are preferable with respect to flexibility, and among the amorphous resins, elastomer resins are preferable. In particular, since elastomer resins do not suffer deterioration of wearing comfort and are able to be stitched like knit or woven fabrics, they are preferable.

The above mentioned amorphous resins include various kinds of amorphous resins. Particularly amorphous resins with JIS A hardness of 50–90 are preferable because amorphous resins with a hardness in this range have a proper flexibility without wearing discomfort while providing supporting force, further improving the ankle sprain prevention effect. "JIS" is the abbreviation for the Japanese Industrial Standard. "JIS A hardness" of 50–90 roughly corresponds with the "Shore hardness D" (ASTM D2240) of 12–38.

Examples of amorphous resins include amorphous polyamide type copolymer resins, amorphous ethylene-vinyl acetate type copolymer resins, amorphous olefin-stylene type copolymer resins, amorphous polybutylene-terephthalate type copolymer resins, amorphous olefin type copolymer resins and polyethylenes. In particular, elastomer resins such as chemically crosslinked elastomer resins (vulcanized types) and physically crosslinked elastomer resins (thermoplastic elastomers).

Preferable examples of the elastomer resins include polystyrene type elastomer resins, polyolefine type elastomer resins such as "MILASTOMER" made by MITSUI PETROCHEMICAL INDUSTRIES, LTD., polyester type elastomer resins, polyurethane type elastomer resins, polyamide type elastomer resins and silicone type elastomer resins. A blend of two or more of the above mentioned resins can be used as well.

In particular, since a bone of such resins can be directly stitched to the lower leg protection garment with a sewing machine, it is preferable. The method of mounting a bone to the lower leg protection garment is not limited to stitching but various conventional methods used for mounting a bone to a garment can be used, such as adhesion including adhesion with an adhesive, heat adhesion, high frequency adhesion, and securing by containing in a French seam formed with a bias tape stitched along the circumference.

The lower leg protection garment of the present invention comprises a portion with a strong straining force which covers at least a part of tuber calcaneus across the sole and extends to the vicinity of the region just below the knee joint covering at least a part of the both sides of the lower leg region, and thus the portion with a strong straining force extends from at least a part of tuber calcaneous to the vicinity of the region just below the knee joint to provide a force to firmly lift upward and stabilize the heel, and provides a lower leg protection garment which prevents the inversion and the eversion of the ankle to provide the sprain prevention effect. The present garment enables easy wearing like putting on socks to the proper orientation for having the tube-like shape at least from the vicinity of the region just below the knee joint to the vicinity of the ankle, without the skill required in taping treatments such as the skill to know the portion to adhere or the portion to strongly adhere without the risk of the blood circulation disorder or nervous disorder caused by strongly applying taping. The present garment has good wearing comfort since at least one third of the area in the portion having a tube-like shaped below the knee joint is formed with a portion with a weak straining force, allowing the easy extention of the material to put on and not compressing the leg region strongly unlike an embodiment comprising the whole portion with a portion with a strong force.

A portion with a strong straining force covers at least a part of tuber calcaneus across the sole and extends to the vicinity of the region just below the knee joint avoiding the malleolus medialis and a malleolus lateralis in the preferable embodiment of the lower leg protection garment of the present invention. Thus, a lower leg protection garment providing further better wearing comfort by preventing friction between the malleolus region and the protection garment having a portion with a strong straining force compressing the malleolus region during sports activities can be provided.

A portion with a strong straining force covers at least a part of the tuber calcaneus across the sole and extends to the vicinity of the region just below the knee joint along the vicinity of the both sides of the motor point of the gastrocnemius longitudinally, and the portion to cover the motor point of the gastocnemius is formed with the portion with the weak straining force in the preferable embodiment of the lower leg protection garment of the present invention. Thus, the lower leg protection garment provides further good wearing comfort by reinforcing the lower leg region to prevent the occurence or relapse of ankle sprain without disturbing the movements such as contraction of the gastrocnemius, which is the most projecting muscle among the muscles of the lower leg region, and allows anybody to put on te garment easily in the proper orientation.

Since the preferable embodiment of the lower leg protection garment of the present invention comprises a portion with a weak straining force on the central part of the Achilles' tendon, a lower leg protection garment providing a further better wearing comfort by reinforcing the lower leg region to prevent the occurence or relapse of the ankle sprain without disturbing the movements of the Achilles' tendon, while allowing anybody to put on the garment easily in the proper orientation, can be provided.

A tube-like portion with a strong straining force further covers at least a part of the plantar arch across the sole and extends to at least a part of the dorsum pedis so that the portion with the strong straining force forms a further tube-like part, and the width of the tube-like part with the strong straining force at the sole is 3 cm or more in the preferable embodiment of the lower leg protection garment of the present invention. Thus, a lower leg protection garment further having the function of preventing the inflammation of plantar fascia, by having the portion at the plantar arch with a strong straining force of at least 3 cm width, can be provided.

Since a portion with a strong straining force further covers the front side of the ankle so that the portion with the strong straining force forms a further tube-like part in the preferable embodiment of the lower leg protection garment of the present invention, a lower leg protection garment providing a further reinforced sprain prevention effect by firmly holding and stabilizing the ankle can be provided. Also, since a portion with a strong straining force further covers at least a part of the plantar arch across the sole with a width at the sole of at least 3 cm, and extends to cover at least a part of the dorsum pedis to form a further tube-like shape, and extends further from the dorsum pedis to the front side of the ankle to cover the ankle to form a tube-like shape in the preferable embodiment of the lower leg protection garment of the present invention, a lower leg protection garment providing effective prevention effect of the inflammation of plantar fascia, holding the ankle firmly, providing reinforced sprain prevention effect can be provided.

Since support bones are further provided on at least a part of heel bone, or the vicinity of the ankle in the lower leg region in the preferable embodiment of the lower leg protection garment of the present invention, avoiding the malleolus medialis and the malleolus lateralis regions, a lower leg protection garment providing further reinforced sprain prevention effect by fixing the heel or the ankle region further firmly can be provided.

Since the straining force of the portion with a strong straining force is in the range of 100 to 400 gf in the preferable embodiment of the lower leg protection garment of the present invention, a lower leg protection garment with a well balanced protection effect of the lower leg region and good wearing comfort can be provided. A strong straining force in the above mentioned range is an appropriate straining force to provide the sprain prevention protection effect but is not too strong in terms of wearing comfort can be provided. Since the straining force of the portion with a weak straining force is in the range of 30 to 250 gf in the preferable embodiment of the lower leg protection garment of the present invention, a lower leg protection garment which does not disturb the muscle movements of the region covered with the portion with a weak straining force, allows easy expansion of the garment at wearing by not having a too strong straining force, without susceptibility of loosening the garment at wearing by not having a too weak straining force can be provided.

When the main body comprises a material with a weak straining force, and a material with a strong straining force is further superimposed to the surface and/or the underside of the material with a weak straining force to provide a portion with a strong straining force in the preferable embodiment of the lower leg protection garment of the present invention, a lower leg protection garment which can be easily produced can be provided. The garment can be produced by only forming a base material of the protection garment main body with a material with a weak straining force, and fixing a material with a strong straining force to the surface and/or the underside of the base material in the necessary region by an appropriate means such as stitching or adhesion without the complicated, and the time taking operation of alternately seaming a portion with a weak straining force and a portion with a strong straining force can be avoided.

According to the preferable embodiment of the lower leg protection garment of the present invention, a portion with a weak straining force comprises an all ways stretch tricot. Since the all ways stretch tricot is a knit fabric thinner than pile fabric or neoprene used in conventional supporters, a lower leg protection garment having a soft fittability, capable of following the stretch of the skin, being lightweight, with a better feeling and ventilation, easily put on to a leg region for easy expansion at wearing, and relatively adjustable to the variation of the size of the lower leg region of a wearer can be provided.

According to the preferable embodiment of the lower leg protection garment of the present invention, the main body comprises a material with a weak straining force and a material with a strong straining force is further superimposed to the surface and/or the underside of the material with a weak straining force to provide a portion with a strong straining force wherein the material with a weak straining force comprises an all ways stretch tricot. Thus, a lower leg protection garment which can be easily produced by only forming a base material of the protection garment main body with a material with a weak straining force, and fixing a material with a strong straining force to the surface and/or the underside of the base material in the necessary region by an appropriate means such as stitching or adhesion without the time-consuming operation of alternately seaming a portion with a weak straining force and a portion with a strong straining force, and which further provides a soft fittability, capable of following the stretch of the skin, being of light weight, with a better feeling and ventilation, easily put on to a leg region for easy expansion at wearing, and relatively adjustable to the variation of the size of the lower leg region of a wearer, can be provided.

According to the preferable embodiment of the lower leg protection garment of the present invention, a portion with a strong straining force comprises a spandex power net. Since the spandex power net is a knit fabric much thinner than pile fabric or neoprene used in conventional supporters and can provide a straining force sufficient for a portion with a strong straining force, a lower leg protection garment having a good fittability, a light weight, without disturbing the movements of the muscle, with a better feeling can be provided. Further, since the material is thin, unlike a thick fabric which may have wrinkles when bending an ankle in the bent region to compress the joint region with the thickness of the wrinkles to arise problems such as preventing bending of the joint or causing wearing discomfort, a lower leg protection garment which provides good wearing comfort without disturbing necessary physical movements can be provided.

When a crotch portion is further provided to form a pants-like shape in the preferable embodiment of the lower leg protection garment of the present invention, a lower leg protection garment which can be put on easily with an operation like putting on pants, in the desired position and the appropriate orientation can be obtained. Such a garment has reduced risk of sliding down during physical movements by having the waist portion to be secured to the user's waist, unlike protection garments having the length only to the lower leg region or to the thigh region.

What is claimed is:

1. A lower leg protection garment to be compressingly worn on a surface of a human body, having a tube shape that extends in use from the vicinity of a region just below a user's knee joint to the vicinity of a user's ankle, comprising a portion with a strong straining force which in use covers at least part of a user's tuber calcaneus across a user's sole and extends to the vicinity of the region just below the knee joint, avoiding a user's malleolus medialis and malleolus lateralis, covering at least a part of both sides of a user's lower leg region and covering longitudinally regions along the vicinity of both sides of a motor point of a user's gastrocnemius, and further comprising a portion with a weak straining force that forms at least one third of the tube shape below the knee joint, the motor point of the user's gastrocnemius being covered in use by the portion with a weak straining force.

2. A pants-like garment, comprising a pair of legs joined by a crotch portion, each of the legs comprising a lower leg protection member having a tube shape that extends in use from the vicinity of a region just below a user's knee joint to the vicinity of a user's ankle, the lower leg protection member comprising a portion with a strong straining force which in use covers at least part of a user's tuber calcaneus across a user's sole and extends to the vicinity of the region just below the knee joint, avoiding a user's malleolus medialis and malleolus lateralis, covering at least a part of both sides of a user's lower leg region and covering longitudinally regions along the vicinity of both sides of a motor point of a user's gastrocnemius, the lower leg protection member further comprising a portion with a weak straining force that forms at least one third of the tube shape below the knee joint, the motor point of the user's gastrocnemius being covered in use by the portion with a weak straining force.

3. The lower leg protection garment according to claim 1, wherein a portion which in use covers a central part of a user's Achilles' tendon has a weak straining force.

4. The lower leg protection garment according to claim 1, wherein the portion with a strong straining force further covers in use at least a part of a user's plantar arch across the sole extending to at least a part of the dorsum pedis so that the portion with the strong straining force forms a further tube-like part, and the portion with the strong straining force has the width at the sole of 3 cm or more.

5. The lower leg protection garment according to claim 1, wherein the portion with a strong straining force further covers the front side of the ankle, so that the portion with the strong straining force forms a further tube-like part.

6. The lower leg protection garment according to claim 1, wherein the portion with a strong straining force further covers in use at least a part of the plantar arch across the sole with a width at the sole of at least 3 cm and extends to at least a part of the dorsum pedis so that the portion with the strong straining force forms a further tube-like part, and extends further from the dorsum pedis to the front side of the ankle to cover the ankle so that the portion with the strong straining force forms a further tube-like part.

7. The lower leg protection garment according to claim 1, further comprising support bones, positioned in use in the area of the heel bone, or the vicinity of the ankle in the lower leg region, avoiding the malleolus medialis and the malleolus lateralis regions.

8. The lower leg protection garment according to claim 1, wherein the straining force of the portion with a strong straining force is in the range of 100 to 400 gf.

9. The lower leg protection garment according to claim 1, wherein the straining force of the portion with a weak straining force is in the range of 30 to 250 gf.

10. The lower leg protection garment according to claim 1, wherein the main body comprises a material with a weak straining force, and a material with a strong straining force is further superimposed on at least one selected from the group consisting of the surface and the underside of the material with a weak straining force to provide a portion with a strong straining force.

11. The lower leg protection garment according to claim 1, wherein the portion with a weak straining force is an all ways stretch tricot.

12. The lower leg protection garment according to claim 10, wherein the material with a weak straining force is an all ways stretch tricot.

13. The lower leg protection garment according to claim 1, wherein the portion with a strong straining force is a spandex power net.

* * * * *

UNITED STATES PATENT AND TRADEMARK OFFICE
CERTIFICATE OF CORRECTION

PATENT NO. : 5,640,714

DATED : June 24, 1997

INVENTOR(S) : Tanaka

It is certified that error appears in the above-identified patent and that said Letters Patent is hereby corrected as shown below:

In column 10, line 53, insert --is-- after the word "6(b)".

In column 10, line 57, insert --a-- after the word "with".

In column 13, line 32, "lee" should read --leg--.

In column 13, line 54, delete "the" after the word "has".

In column 18, line 40, "te" should read --the--.

In column 21, line 5, claim 2, insert --:-- after the word "comprising".

Signed and Sealed this

Third Day of March, 1998

*Attest:*

BRUCE LEHMAN

*Attesting Officer*  *Commissioner of Patents and Trademarks*